(12) United States Patent
Kato et al.

(10) Patent No.: US 10,395,091 B2
(45) Date of Patent: Aug. 27, 2019

(54) IMAGE PROCESSING APPARATUS, IMAGE PROCESSING METHOD, AND STORAGE MEDIUM IDENTIFYING CELL CANDIDATE AREA

(71) Applicant: FUJIFILM CORPORATION, Tokyo (JP)

(72) Inventors: Noriji Kato, Yokohama (JP); Yukio Kumazawa, Yokohama (JP); Hideto Oda, Yokohama (JP); Ryota Ozaki, Yokohama (JP)

(73) Assignee: FUJIFILM CORPORATION, Tokyo (JP)

( * ) Notice: Subject to any disclaimer, the term of this patent is extended or adjusted under 35 U.S.C. 154(b) by 58 days.

(21) Appl. No.: 14/830,157

(22) Filed: Aug. 19, 2015

(65) Prior Publication Data

US 2015/0356342 A1    Dec. 10, 2015

Related U.S. Application Data

(63) Continuation of application No. PCT/JP2013/081012, filed on Nov. 18, 2013.

(30) Foreign Application Priority Data

May 31, 2013    (JP) ................. 2013-115443

(51) Int. Cl.
*G06K 9/00*    (2006.01)
*G06K 9/62*    (2006.01)
(Continued)

(52) U.S. Cl.
CPC ......... *G06K 9/00134* (2013.01); *C12M 41/36* (2013.01); *G01N 33/5005* (2013.01);
(Continued)

(58) Field of Classification Search
CPC ............ G06K 9/00134; G06K 9/0014; G06K 9/6262; G06K 9/6269; C12M 41/36; G01N 33/5005; G06T 7/0083; G06T 2207/30024
See application file for complete search history.

(56) References Cited

U.S. PATENT DOCUMENTS 5,313,532 A *  5/1994  Harvey .................. G06K 9/32
                                                     382/133
6,859,802 B1   2/2005  Rui
(Continued)

FOREIGN PATENT DOCUMENTS

JP    H07-319681 A     12/1995
JP    2009-237640 A    10/2009
(Continued)

OTHER PUBLICATIONS

Apr. 29, 2016 Office Action issued in Chinese Patent Application No. 201380075656.3.
(Continued)

*Primary Examiner* — Vincent Rudolph
*Assistant Examiner* — Pinalben Patel
(74) *Attorney, Agent, or Firm* — Oliff PLC

(57) ABSTRACT

An image-feature-value calculating unit extracts an image feature value of an image of a cell candidate area. An NRBC discriminating unit uses a pre-trained discriminator to identify whether or not a target cell is shown in the cell candidate area, on the basis of the image feature value of the image of the cell candidate area. When the cell candidate area is identified as an area in which a target cell is shown, a discrimination result display unit displays the image of the cell candidate area. When the cell candidate area is identified as an area in which a target cell is shown, a discriminator training unit trains the discriminator by using the image feature value of the image of the cell candidate area as a (Continued)

training sample on the basis of a user input about whether or not a target cell is shown in the cell candidate area.

6 Claims, 7 Drawing Sheets

(51) Int. Cl.
    *G01N 33/50* (2006.01)
    *C12M 1/34* (2006.01)
    *G06T 7/12* (2017.01)

(52) U.S. Cl.
    CPC ......... *G06K 9/0014* (2013.01); *G06K 9/6262* (2013.01); *G06K 9/6269* (2013.01); *G06T 7/12* (2017.01); *G06T 2207/30024* (2013.01)

(56) References Cited

U.S. PATENT DOCUMENTS

| | | | | |
|---|---|---|---|---|
| 7,958,063 | B2* | 6/2011 | Long | G06K 9/00147 706/12 |
| 8,908,945 | B2* | 12/2014 | Santamaria-Pang | G06K 9/34 382/128 |
| 9,576,181 | B2* | 2/2017 | Allano | G06K 9/00127 |
| 2008/0253611 | A1 | 10/2008 | Kennedy et al. | |
| 2010/0254589 | A1* | 10/2010 | Gallagher | G06K 9/0014 382/133 |
| 2011/0286654 | A1* | 11/2011 | Krishnan | G06T 7/0083 382/133 |
| 2014/0092228 | A1 | 4/2014 | Usuba et al. | |
| 2015/0086103 | A1* | 3/2015 | Tsunomori | G06T 7/0012 382/133 |
| 2015/0204771 | A1* | 7/2015 | Sun | G06T 7/0012 382/134 |
| 2015/0213599 | A1* | 7/2015 | Buzaglo | G06T 7/0012 382/128 |
| 2016/0155239 | A1* | 6/2016 | Aragaki | G02B 21/367 382/103 |
| 2017/0169567 | A1* | 6/2017 | Chefd'hotel | G06K 9/00127 |
| 2017/0270666 | A1* | 9/2017 | Barnes | G16H 50/30 |

FOREIGN PATENT DOCUMENTS

| | | |
|---|---|---|
| JP | 4346923 B2 | 10/2009 |
| JP | 2011-28436 A | 2/2011 |
| JP | 2012-080802 A | 4/2012 |
| JP | 2012-254042 A | 12/2012 |
| JP | 2012254042 A * | 12/2012 |
| WO | 00/049391 A1 | 8/2000 |
| WO | 2012-091056 A1 | 7/2012 |
| WO | 2012/169088 A1 | 12/2012 |

OTHER PUBLICATIONS

Aoki, Kosuke et al., "Auto-Detection of Nucleated Red Blood Cells from Massive Microscopy Images," The Journal of the Institute of Image Electronics Engineers of Japan, vol. 37, No. 5, (2008), pp. 609-616.

Suzuki, Wakako et al., "Enrichment and Automated Detection of NRBC from Maternal Blood," Journal of the Showa Medical Association, vol. 72, No. 4, (2012), pp. 471-478.

Shimizu, Yosuke et al., "Detection and Retrieval of Nucleated Red Blood Cells Using Linear Subspaces," The Journal of the Institute of Image Electronice Engineers of Japan, vol. 40, No. 1, (2011), pp. 67-73.

Feb. 18, 2014 Search Report issued in International Patent Application No. PCT/JP2013/081012.

Jan. 17, 2017 European Search Report issued in 13886123.2.

A. Dorado et al; "Efficient Image Selection for Concept Learning", IEE Proceedings: Vision, Image and Signal Processing Institution of Electrical Engineers, GB, vol. 153, No. 3, Jun. 8, 2006, pp. 263-273.

Yong Rui et al: "Relevance Feedback: A Power Tool for Interactive Content-Based Image Retrieval", IEEE Transactions on Circuits and Systems for Video Technology, vol. 8, No. 5, Sep. 1, 1998, pp. 644-655.

Nov. 2, 2016 Office Action issued in Japanese Patent Application No. 2013-115443.

May 14, 2018 Office Action issued in Chinese Patent Application No. 201380075656.3.

* cited by examiner

FIG. 7

| AREA ID | COORDINATES DATA | | DISPLAY CONDITION | SELECTION CONDITION |
|---|---|---|---|---|
| | POSITION(X,Y) | SIZE | | |
| 0000 | (X1,Y1) | S1 | 0 (NOT DISPLAYED) | 0 (NOT SELECTED) |
| 0001 | (X2,Y2) | S2 | 0 (NOT DISPLAYED) | 0 (NOT SELECTED) |
| 0002 | (X3,Y3) | S3 | 0 (NOT DISPLAYED) | 0 (NOT SELECTED) |
| 0003 | (X4,X4) | S4 | 0 (NOT DISPLAYED) | 0 (NOT SELECTED) |
| ... | ... | ... | ... | ... |

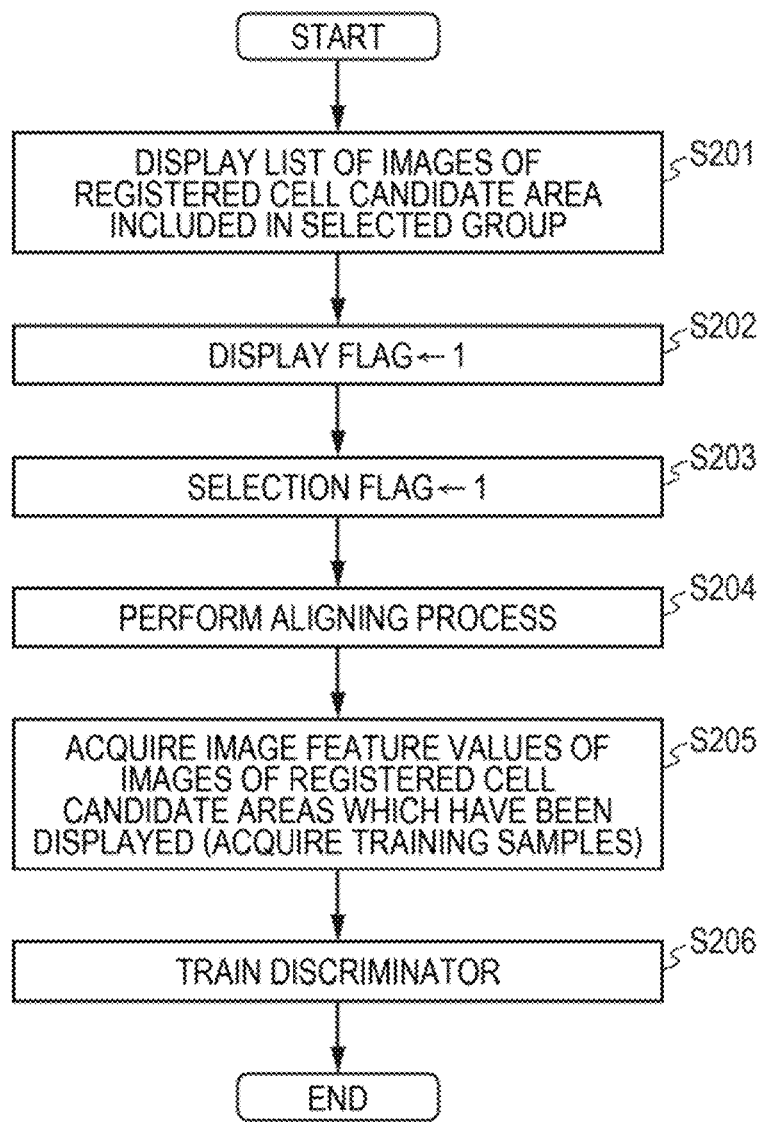

IMAGE PROCESSING APPARATUS, IMAGE PROCESSING METHOD, AND STORAGE MEDIUM IDENTIFYING CELL CANDIDATE AREA

CROSS REFERENCE TO RELATED APPLICATION

This is a continuation of International Application No. PCT/JP2013/081012 filed on Nov. 18, 2013, and claims priority from Japanese Patent Application No. 2013-115443, filed on May 31, 2013.

BACKGROUND

1. Technical Field

The present invention relates to an it processing apparatus, an image processing method, and a storage medium.

2. Related Art

When a diagnosis for a prenatal fetus is to be made, an infinitesimal number of fetus-derived nucleated red blood cells (NRBCs, hereinafter referred to as target cells) contained in maternal blood are detected and used. Since the number of NRBCs which are present in maternal blood is extremely small, visual detection of NRBCs is a burdensome process.

SUMMARY

An aspect of the present invention provides an image processing apparatus including a feature value extracting unit, a discriminating unit, a display unit, an accepting unit, and a discriminator training unit. The feature value extracting unit extracts an image feature value of an image of a cell candidate area in a captured image obtained by capturing an image of a sample including a target cell. The discriminating unit uses a pre-trained discriminator to identify whether or not the target cell is shown in the cell candidate area, on the basis of the image feature value of the image of the cell candidate area. When the cell candidate area is identified as an area in which the target cell is shown, the display unit displays the image of the cell candidate area. When the cell candidate area is identified as an area in which the target cell is shown, the accepting unit accepts a user input from a user about whether or not the target cell is shown in the cell candidate area. When the cell candidate area is identified as an area in which the target cell is shown, the discriminator training unit trains the discriminator by using the image feature value of the image of the cell candidate area as a training sample on the basis of the user input accepted by the accepting unit.

BRIEF DESCRIPTION OF THE DRAWINGS

Exemplary embodiment(s) of the present invention will be described in detail based on the following figures, wherein

FIG. 7 is a diagram illustrating example information stored in a cell coordinates database;

FIG. 9 is a flowchart illustrating an example process performed by the image processing apparatus.

DETAILED DESCRIPTION

Exemplary embodiment(s) of the present invention will be described in detail below on the basis of the drawings.

Figure 1:
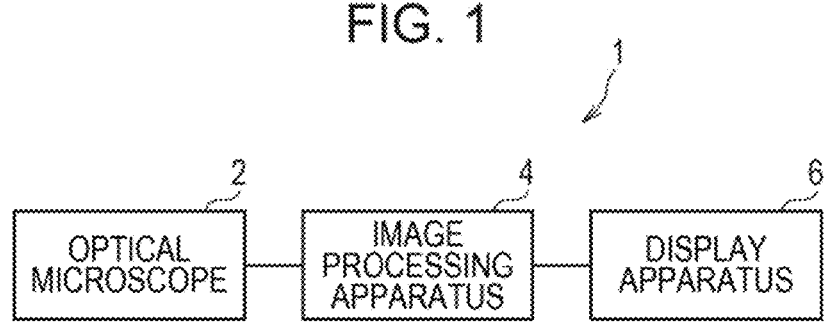
FIG. 1 is a system configuration diagram of an image processing system according to an embodiment.

FIG. 1 is a system configuration diagram of an image processing system 1 according to the present embodiment. As illustrated in FIG. 1, the image processing system 1 includes an optical microscope 2, an image processing apparatus 4, and a display apparatus 6. The image processing apparatus 4 is connected to the optical microscope 2 and the display apparatus 6 which are capable of performing data communication with the image processing apparatus 4.

The optical microscope 2 captures an image of a specimen on slide glass disposed on a platform, by using a CCD camera via an optical system such as an objective lens. In the present embodiment, the specimen is obtained by applying maternal blood to the slide glass and treating the applied maternal blood with May-Giemsa staining. Thus, fetus-derived nucleated red blood cells in the maternal blood are stained bluish purple. The nucleated red blood cells are hereinafter referred to as target cells.

Figure 2:
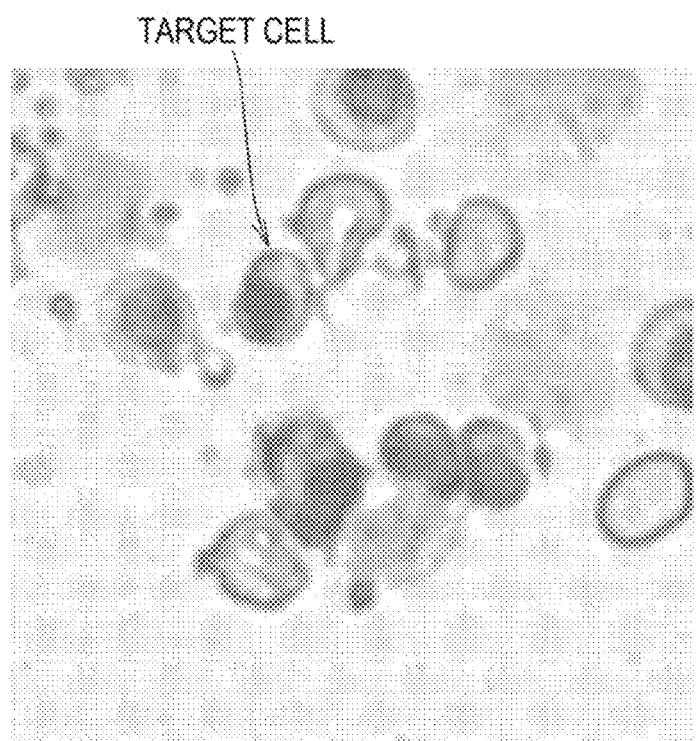
FIG. 2 is a diagram illustrating an example test image.

The image processing apparatus 4 which is, for example, a personal computer obtains a captured image (hereinafter referred to as a test image) obtained by capturing an image by using the optical microscope 2. FIG. 2 illustrates an example test image. As illustrated in FIG. 2, the test image includes images of various cells contained in the maternal blood. A cell having a nucleus stained in a dark color is a target cell. The nucleus of a target cell (nucleated red blood cell) is stained with May-Giemsa staining in a color slightly darker than that of another cell.

The image processing apparatus 4 uses a pre-trained discriminator to specify cell candidate areas in which target cells are highly likely to be shown, and displays a list of the images of the specified cell candidate areas on the display apparatus 6.

Figure 3:
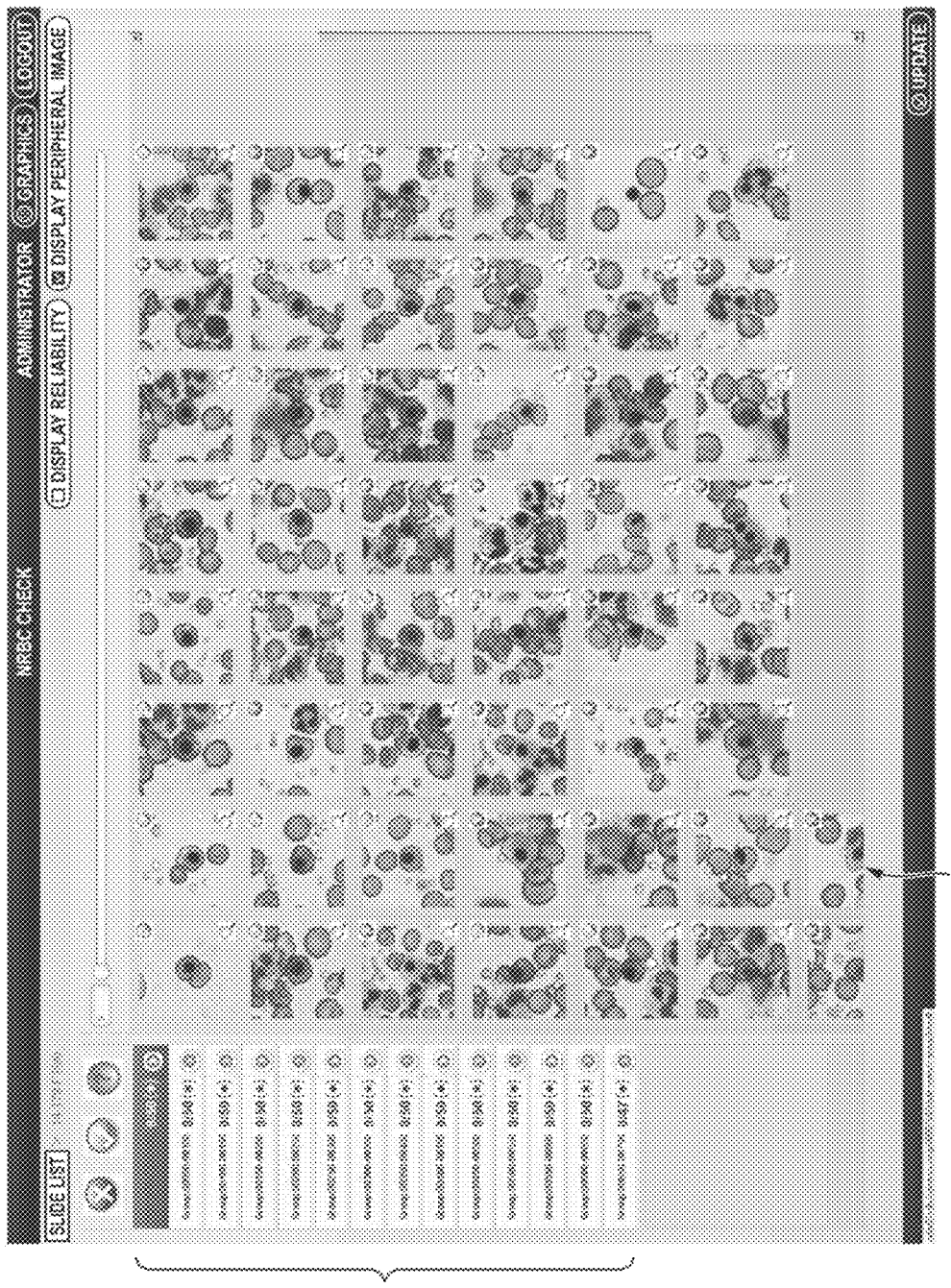
FIG. 3 is a diagram illustrating a screen displayed on a display apparatus.

The display apparatus 6 displays a list of the images of the cell candidate areas specified by the image processing apparatus 4. FIG. 3 is a diagram illustrating an example screen displayed on the display apparatus 6. As illustrated in FIG. 3, a list of the images of the specified cell candidate areas is displayed on the screen. In the present embodiment, the images are grouped into a predetermined number of groups. A list of images belonging a group selected from the groups is displayed. In this example, multiple buttons 7 corresponding to the groups are displayed in a left end portion of the screen. A list of images belonging to a group corresponding to a button 7 clicked by a user (for example, a doctor carrying out an inspection) of the image processing apparatus 4 is displayed.

When the user is to make a prenatal diagnosis, the user carries out a cell inspection while referring to the screen. That is, the user views each of the images displayed on the screen. The user selects an image determined to be an image in which a target cell is shown, among the images displayed on the screen. For example, the user clicks an image determined to be an image in which a target cell is shown.

Thus, the user achieves the focus of the objective lens to the vicinity of the cell shown in the selected image, and starts extracting the target cell.

As described above, the discriminator is used to specify the cell candidate areas in which target cells are highly likely to be shown. In the image processing system 1, training samples are automatically obtained in the process of a cell inspection described above, and the discriminator is trained by using the training samples. Therefore, the user does not necessarily perform an operation for obtaining training samples, separately from the cell inspection operation.

A technique for enabling the discriminator to be trained in the process of a cell inspection operation will be described.

Figure 4:
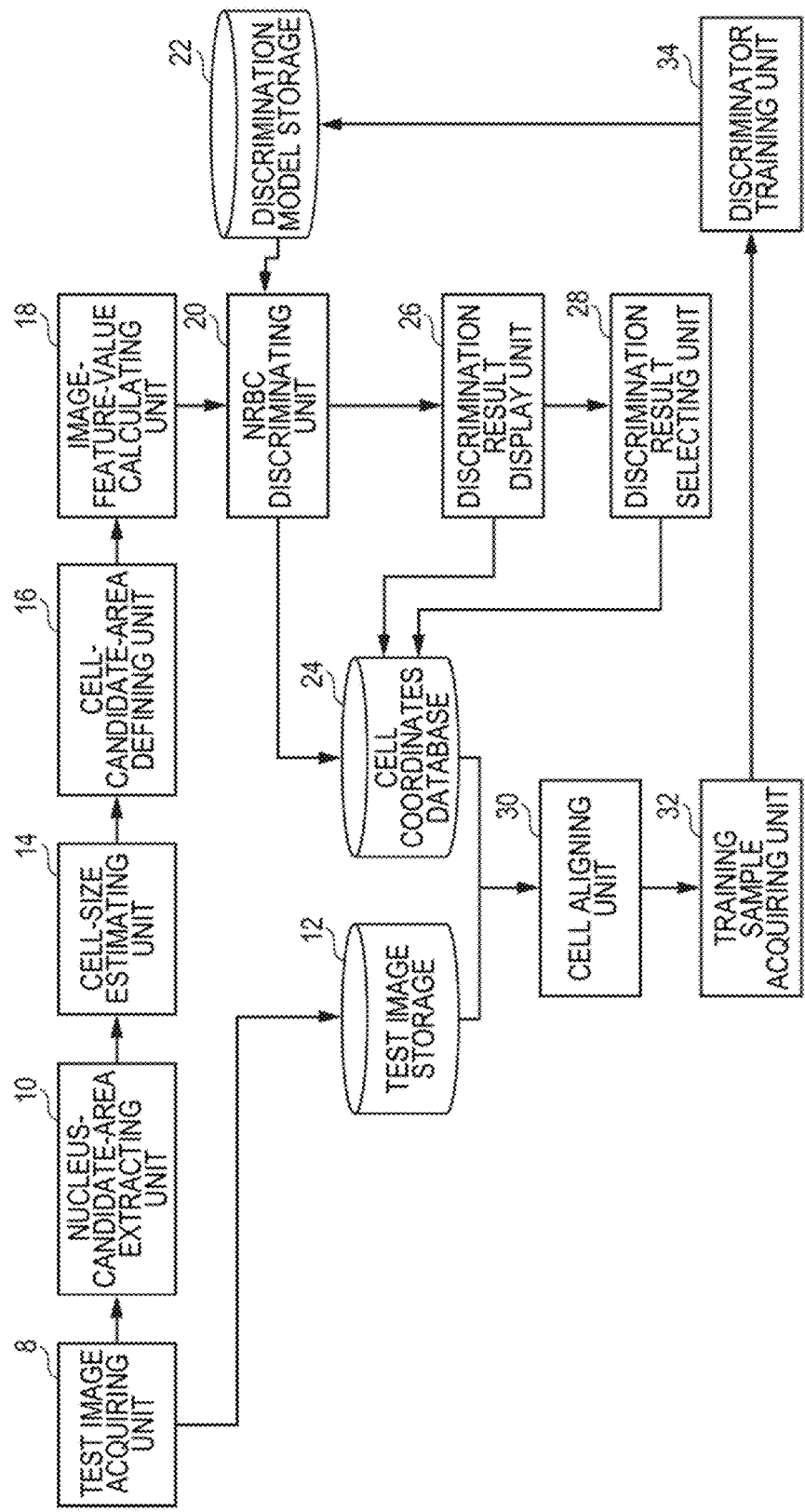
FIG. 4 is a functional block diagram illustrating functions implemented in n image processing apparatus.

FIG. 4 is a functional block diagram illustrating functions implemented in the image processing apparatus 4. In the image processing apparatus 4, a test image acquiring unit 8, a nucleus-candidate-area extracting unit 10, a test image storage 12, a cell-size estimating unit 14, a cell-candidate-area defining unit 16, an image-feature-value calculating unit 18, an NRBC discriminating unit 20, a discrimination model storage 22, a cell coordinates database 24, a discrimination result display unit 26, a discrimination result selecting unit 28, a cell aligning unit 30, a training sample acquiring unit 32, and a discriminator training unit 34 are implemented. These functions are achieved in such a manner that a computer including a control unit such as a microprocessor, a memory unit such as a memory, an input/output unit for receiving/transmitting data from/to an external device such as an operation accepting unit for accepting a user operation, and the like reads programs stared in a computer-readable information storage medium (for example, an optical disk, a magnetic disk, a magnetic tape, a magneto-optical disk, or a flash memory) and executes the programs. The programs may be supplied to the image processing apparatus 4 which is the computer, via a data communication network such as the Internet.

The functions will be described below. The test image acquiring unit 8 acquires data of a test image (see FIG. 2) captured by using the optical microscope 2, from the optical microscope 2, and stores the test image in the test image storage 12.

Figure 5:
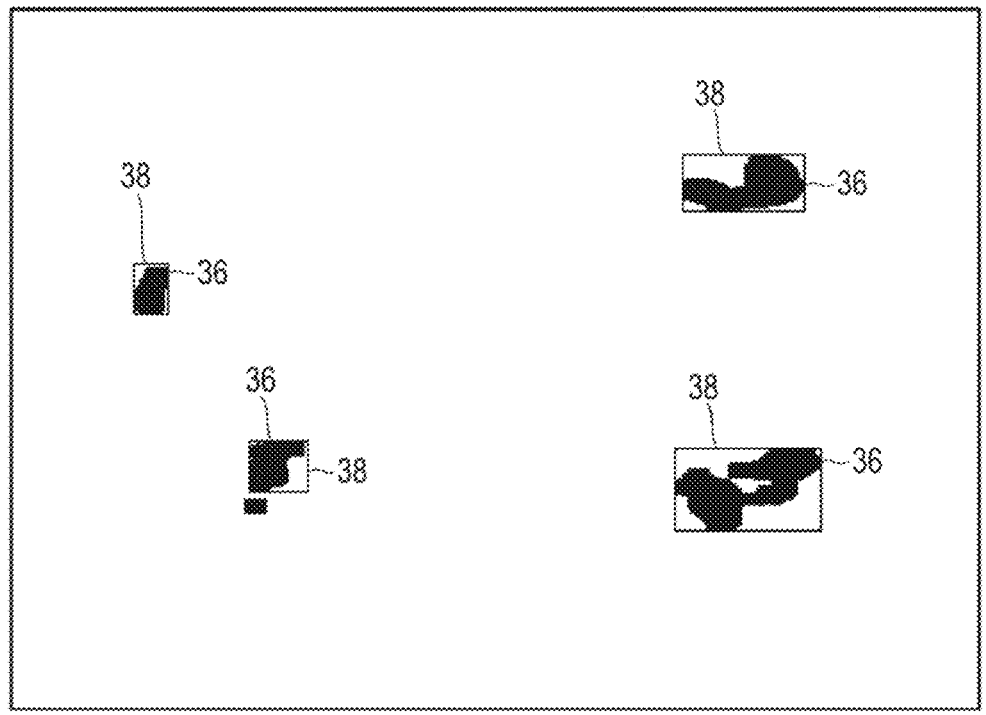
FIG. 5 is a diagram illustrating an example of pixel clusters and nucleus candidate areas.

The nucleus-candidate-area extracting unit 10 extracts nucleus candidate areas corresponding to the nuclei of target cells, from the test image. For example, the nucleus-candidate-area extracting unit 10 extracts pixel clusters having significant pixels from the test image. A significant pixel is a pixel whose pixel value (RGB value) falls within a predetermined range. The nucleus-candidate-area extracting unit 10 extracts a circumscribed rectangular area of each of the pixel dusters as a nucleus candidate area. FIG. 5 illustrates an example of pixel clusters 36 and nucleus candidate areas 38 which are extracted from the test image. A black portion indicates a pixel cluster 36.

The cell-size estimating unit 14 estimates a range (rectangular area) of a cell size by using a predetermined relational expression from a projection size obtained when a nucleus candidate area 38 extracted by the nucleus-candidate-area extracting unit 10 is projected to the slide glass surface.

Figure 6:
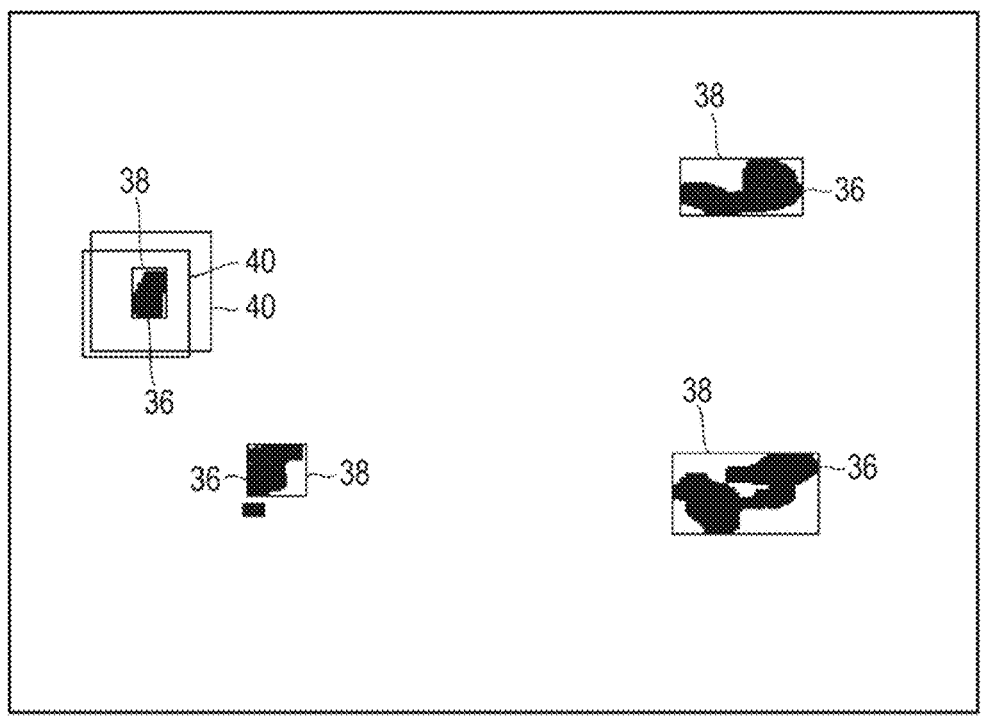
FIG. 6 is a diagram illustrating example cell candidate areas.

The cell-candidate-area defining unit 16 defines multiple cell candidate areas described above which are likely to contain target cells, on the basis of a nucleus candidate area 38. That is, the cell-candidate-area defining unit 16 defines multiple rectangular areas, in each of which a point in the nucleus candidate area 38 is located at the center and each of which has a size in the range estimated by the cell-size estimating unit 14, as cell candidate areas. FIG. 6 illustrates example cell candidate areas 40. In FIG. 6, the cell candidate areas 40 are illustrated, in each of which a point of a nucleus candidate area 38 is located at the center.

For each of the cell candidate areas 40, the image-feature-value calculating unit 18 extracts an image feature value from the image of the cell candidate area 40. In this example, it is assumed that a HOG (Histograms of Oriented Gradients) feature value is calculated as an image feature value. However, any information may be used as an image feature value as long as the information describes an image feature. The image-feature-value calculating unit 18 may extract an image feature value from an enlarged or reduced image of the cell candidate area 40.

For each of the cell candidate areas 40, the NRBC discriminating unit 20 identifies whether or not a target cell is shown in the cell candidate area 40, on the basis of the image feature value of the image of the cell candidate area 40 by using the pre-trained discriminator. Examples of the discriminator include an AdaBoost discriminator and a support vector machine. Model parameters for the discriminator are read out from the discrimination model storage 22.

The NRBC discriminating unit 20 registers a cell candidate area 40 identified as an area in which a target cell is shown, in the cell coordinates database 24. FIG. 7 illustrates example information stored in the cell coordinates database 24. As illustrated in FIG. 7, the cell coordinates database 24 includes an area ID field, a coordinates data field, a display condition field, and selection condition field. The NRBC discriminating unit 20 stores the ID of a cell candidate area 40 identified as an area in which a target cell is shown, in the area ID field. The NRBC discriminating unit 20 stores coordinates data representing a cell candidate area 40 identified as an area in which a target cell is shown, in the coordinates data field in association with the ID of the cell candidate area 40. The coordinates data includes the coordinates of the position of a representative point (for example, the center or the upper left vertex) of a cell candidate area 40 and the size (length of one side) of the cell candidate area 40.

The NRBC discriminating unit 20 stores the value of a display flag indicating whether or not the image of a cell candidate area 40 identified as an area in which a target cell is shown has been displayed, in the display condition field in association with the ID of the cell candidate area 40. The value "0" indicates that the image of the cell candidate area 40 has not been displayed, and the value "1" indicates that the image of the cell candidate area 40 has been displayed. In other words, the value "0" indicates that a user has not viewed the image of the cell candidate area 40, and the value "1" indicates that the user has viewed the image of the cell candidate area 40. At first, the value "0" is stored. The NRBC discriminating unit 20 stores the value of a selection flag indicating whether or not a user has selected the image of a cell candidate area 40 identified as an area in which a target cell is shown, in the selection condition field in association with the ID of the cell candidate area 40. The value "0" indicates that the image of the cell candidate area 40 has not been selected, and the value "1" indicates that the image of the cell candidate area 40 has been selected. In other words, the value "0" indicates that the user has determined that a target cell is not shown in the cell candidate area 40, and the value "1" indicates that the user has determined that a target cell is shown in the cell candidate area 40. At first, the value "0" is stored.

Description will be continued by referring to a cell candidate area 40 registered in the cell coordinates database 24 as a registered cell candidate area 40.

The discrimination result display unit 26 displays the images of registered cell candidate areas 40 on the display apparatus 6. In the present embodiment, the registered cell candidate areas 40 registered in the cell coordinates database 24 are grouped into a predetermined number of groups. A list of the images of the registered cell candidate areas 40 belonging to a group selected by a user among the groups is displayed (see FIG. 3). Accordingly, the images of at least some of the registered cell candidate areas 40 registered in the cell coordinates database 24 are displayed.

The discrimination result display unit 26 updates the display flag values associated with the IDs of the registered cell candidate areas 40 displayed on the display apparatus 6, with "1".

The discrimination result selecting unit 28 receives a user input about whether or not a target cell is shown in a registered cell candidate area 40. In the present embodiment, a user input about whether or not a target cell is shown in a registered cell candidate area 40 displayed on the display apparatus 6 is received. Specifically, the discrimination result selecting unit 28 receives selection (in this example, a click on the image of a registered cell candidate area 40), which is made by a user, of at least one of the registered cell candidate areas 40 displayed on the display apparatus 6. The registered cell candidate area 40 determined by the user himself/herself to be an area in which a target cell is shown is selected. The discrimination result selecting unit 28 updates the selection flag value associated with the ID of the registered cell candidate area 40 selected by the user, with "1".

When the user determines that a target cell is shown in a registered cell candidate area 40, the cell aligning unit 30 analyzes the image of the registered cell candidate area 40, and updates the registered cell candidate area 40 on the basis of the analysis result. Specifically, for a registered cell candidate area 40 selected by the user, the cell aligning unit specifies a cell wall area which corresponds to the outline of a cell wall and which is included in the registered cell candidate area 40, according to a known outline extraction algorithm, and updates the registered cell candidate area 40 on the basis of the specified cell wall area. For example, the cell aligning unit 30 may update the registered cell candidate area 40 with a circumscribed rectangular area of the cell wall area. For example, the cell aligning unit 30 may update the registered cell candidate area 40 so that the center of the registered cell candidate area 40 matches the center (centred) of the cell wall area. Alternatively, the registered cell candidate area 40 may be set to a rectangle whose center is located at the centroid of the nucleus candidate area 38 and which contains the cell wall area.

Similarly to the age-feature-value calculating unit 18, the training sample acquiring unit 32 acquires an image feature value of the image of a registered cell candidate area 40. In the present embodiment, the training sample acquiring unit 32 acquires image feature values for the registered cell candidate areas 40 which have been displayed. Specifically, the training sample acquiring unit 32 refers to the cell coordinates database 24 to specify registered cell candidate areas 40 whose display flag values are equal to "1", and extracts the image feature values of the images of the specified registered cell candidate areas 40.

The discriminator training unit 34 uses the image feature values acquired by the training sample acquiring unit 32 as training samples to train the discriminator. Model parameters obtained as a training result are stored in the discrimination model storage 22. The training samples are also called training data.

The discriminator is trained on the basis of the user input received by the discrimination result selecting unit 28. That is, when a user determines that a target cell is shown in a registered cell candidate area 40, the image feature value of the image of the registered cell candidate area 40 acquired by the training sample acquiring unit 32 is used as a positive training sample. That is, the image feature value of the image of a registered cell candidate area 40 whose selection flag value is equal to "1" is used as a positive training sample. In contrast, when the user determines that a target cell is not shown in a registered cell candidate area 40, the image feature value of the image of the registered cell candidate area 40 acquired by the training sample acquiring unit 32 is used as a negative training sample. That is, the image feature value of the image of a registered cell candidate area 40 whose selection flag value is equal to "0" is used as a negative training sample. The discriminator may be trained by using only positive training samples or negative training samples. Alternatively, the discriminator may be trained by using only some of the positive examples and the negative examples.

Thus, in the image processing apparatus 4, the training sample acquiring unit 32 and the discriminator training unit 34 are used to obtain training samples in the process of a cell inspection operation, and to train the discriminator by using the training samples. In addition, the image processing apparatus 4 does not use the images of all of the cell candidate areas 40 as training samples. Only images identified by the NRBC discriminating unit as images containing target cells are used as training samples. Therefore, the discrimination accuracy of the discriminator is improved.

Figure 8:
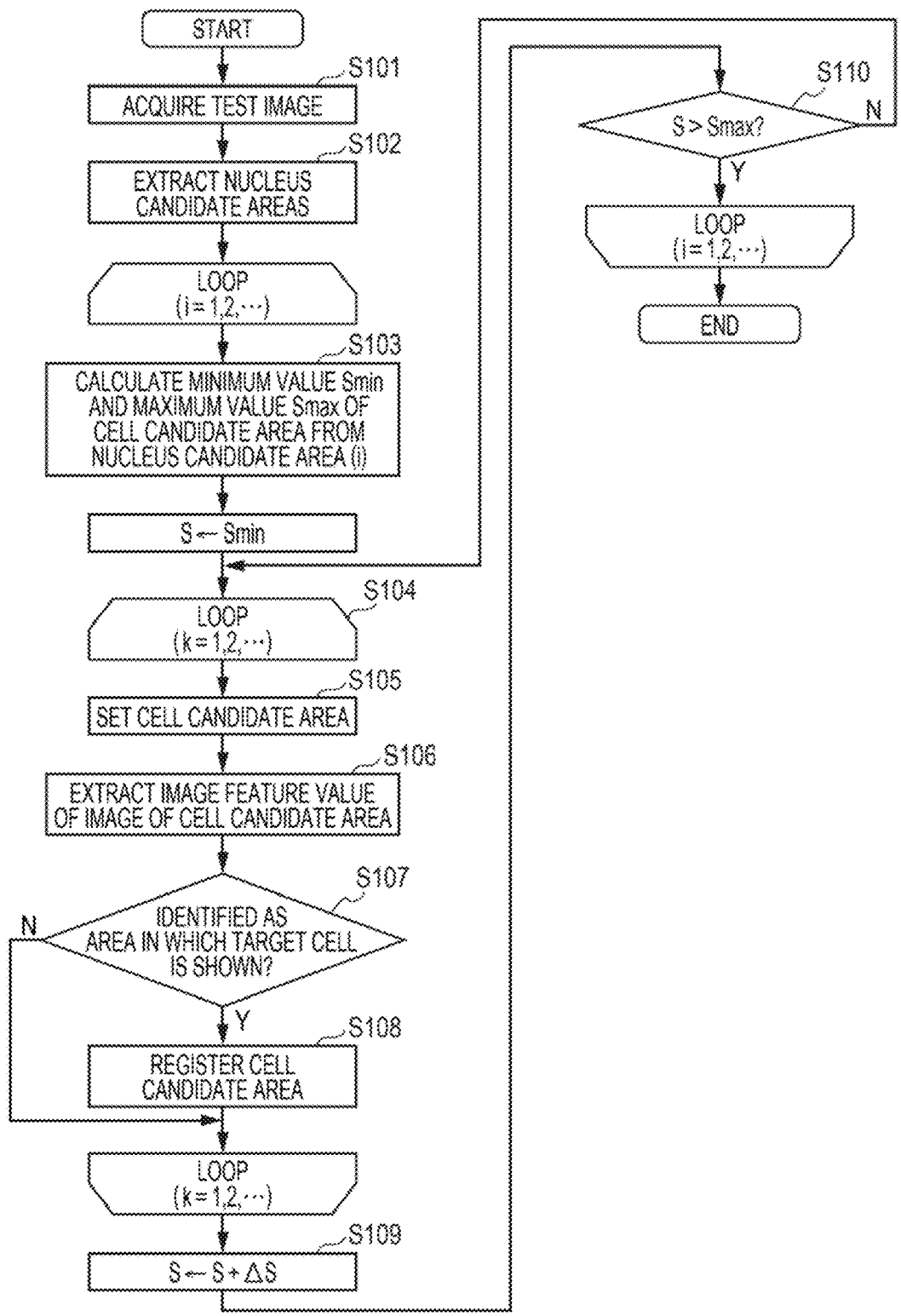
FIG. 8 is a flowchart illustrating an example process performed by the image processing apparatus.

FIGS. 8 and 9 are flowcharts illustrating an example process performed by the image processing apparatus 4. First, FIG. 8 will be described. The image processing apparatus 4 causes the test image acquiring unit 8 to acquire a test image (see FIG. 2) from the optical microscope 2 (S101). The test image is stored in the test image storage 12. The image processing apparatus 4 causes the nucleus-candidate-area extracting unit 10 to extract multiple nucleus candidate areas 38 (S102). That is, in S102, the image processing apparatus 4 generates a binary image obtained by converting the values of pixels in the test image, each of which has an RGB value falling within the predetermined range, into "1" and converting the values of the other pixels into "0". In S102, the image processing apparatus 4 specifies pixel clusters 36 (see FIG. 5) having pixels whose values are equal to "1", and extracts the circumscribed rectangular area for each of the pixel clusters 36 as a nucleus candidate area 38.

The image processing apparatus 4 sequentially selects the nucleus candidate areas 38 one by one as a nucleus candidate area(i), and executes steps S103 to S110 for the nucleus candidate area(i). That is, the image processing apparatus 4 causes the cell-size estimating unit 14 to calculate the minimum value Smin and the maximum value Smax of the size (length of one side) of a cell candidate area 40 according to the predetermined relational expression from the projection size obtained when the nucleus candidate area(i) is projected to the slide glass surface (S103). The image processing apparatus 4 sets the value of the size S for a cell candidate area 40 to the minimum value Smin (S104).

The image processing apparatus 4 sequentially selects pixels one by one in the nucleus candidate area(i) as a pixel(k), and executes steps S105 to S108 for the pixel(k). That is, the image processing apparatus 4 causes the cell-candidate-area defining unit 16 to set a cell candidate area 40 in which the pixel(k) is located at the center and which has a size of S (S105). The image processing apparatus 4 causes the image-feature-value calculating unit 18 to calculate an image feature value of the image of the cell candidate area 40 (S106). For example, in S106, the image processing apparatus 4 calculates the HOG feature value of the image of the cell candidate area 40.

The image processing apparatus 4 causes the NRBC discriminating unit 20 to identify whether or not a target cell is shown in the cell candidate area 40, on the basis of the image feature value calculated in S106 (S107). That is, the image processing apparatus 4 reads the model parameters from the discrimination model storage 22, and causes the discriminator to identify whether or not a target cell is shown in the cell candidate area 40, on the basis of the image feature value calculated in S106. Specifically, in S108, the image processing apparatus 4 inputs the calculated image feature value to the discriminator, and obtains an output value from the discriminator. For example, when the output value is equal to or more than a threshold, the cell candidate area 40 is identified as an area in which a target cell is shown. When the output value is less than the threshold, the cell candidate area 40 is not identified as an area in which a target cell is shown.

If the cell candidate area 40 is identified as an area in which a target cell is shown (Y in S107), the image processing apparatus 4 causes the NRBC discriminating unit 20 to register the cell candidate area 40 into the cell coordinates database 24 (see FIG. 7) (S108). That is, in S108, the image processing apparatus 4 stores a record including the ID of the cell candidate area 40, the coordinates data of the cell candidate area 40, the display flag value "0", and the selection flag value "0", in the cell coordinates database 24. The image processing apparatus 4 executes S105 and its subsequent steps by using the next pixel as the pixel(k). If the cell candidate area 40 is not identified as an area in which a target cell is shown (N in S107), without registering the cell candidate area 40, S105 and its subsequent steps are executed by using the next pixel as the pixel(k).

When steps S105 to S108 are executed for all of the pixels in the nucleus candidate area(i), in S109, the image processing apparatus 4 increments the size S by ΔS (S109), and determines whether or not the incremented size S exceeds Smax (S110). If the incremented size S exceeds Smax (Y in S110), the image processing apparatus 4 uses the next nucleus candidate area 38 as the nucleus candidate area(i) to execute S103 and its subsequent steps. If the incremented size S does not exceed Smax (N in S110), steps S105 to S108 are executed again for all of the pixels in the nucleus candidate area(i).

Through the process illustrated in FIG. 8, multiple cell candidate areas 40 identified as an area in which a target cell is shown are registered in the cell coordinates database 24. The registered cell candidate areas 40 are grouped into a predetermined number of groups.

The process illustrated in FIG. 9 is performed after the process illustrated in FIG. 8. Steps S201 to S203 are executed every time a user selects a group through clicking on a button 7 (see FIG. 3). That is, the image processing apparatus 4 causes the discrimination result display unit 26 to display a list of the images of the registered cell candidate areas 40 included in the group selected by the user, on the display apparatus 6 (S201).

The image processing apparatus 4 causes the discrimination result display unit 26 to update the display flag values for the registered cell candidate areas 40 displayed on the display apparatus, with "1" (S202). Every time the user selects (clicks) the image of any of the registered cell candidate areas 40, the image processing apparatus 4 causes the discrimination result selecting unit 28 to update the selection flag value for the selected registered cell candidate area 40, with "1" (S203).

Step S204 and its subsequent steps are executed, for example, when a user gives a predetermined training instruction. The image processing apparatus 4 causes the cell aligning unit 30 to perform an aligning process (S204). That is, in the aligning process, the image processing apparatus 4 refers to the cell coordinates database 24 to specify a registered cell candidate area 40 whose selection flag value is equal to "1". The test image is read from the test image storage 12, and the image of the registered cell candidate area 40 which has been specified is analyzed according to the known outline extraction algorithm, whereby a cell wall area which corresponds to the outline of a cell wall and which is included in the registered cell candidate area 40 is specified. The registered cell candidate area 40 which has been specified is updated on the basis of the cell wall area. For example, the image processing apparatus 4 may update the registered cell candidate area 40 which has been specified, with a circumscribed rectangular area of the cell wall area. For example, the image processing apparatus 4 may update the registered cell candidate area 40 which has been specified, in such a manner that the center of the registered cell candidate area 40 matches the center (centroid) of the cell wall area. Alternatively, the registered cell candidate area 40 may be updated with a rectangle in which the centroid of the nucleus candidate area 38 is located at the center and which contains the cell wall area. The registered cell candidate area 40 is updated by updating the coordinates data of the registered cell candidate area 40 stored in the cell coordinates database 24.

The image processing apparatus 4 causes the training sample acquiring unit 32 to acquire the image feature values of the images of the registered cell candidate areas 40 which have been displayed (S205). That is, in S205, the image processing apparatus 4 refers to the cell coordinates database 24 to specify registered cell candidate areas 40 whose display flag values are equal to "1", and, similarly to step S106, calculates the image feature values of the images of the registered cell candidate areas 40 which have been specified.

The image processing apparatus 4 causes the discriminator training unit 34 to train the discriminator by using the image feature values obtained in S205 as training samples (S206), and stores model parameters obtained as the training result in the discrimination model storage 22. In the training, the image feature values of the images of registered cell candidate areas 40 whose selection flag values are equal to "1", among the image feature values obtained in S205 are used as positive training samples, and the other image feature values are used as negative training samples.

An embodiment of the present invention is not limited to the above-described embodiment. For example, the case in which a nucleated red blood cell is the target cell is described. A cell other than a nucleated red blood cell may be the target cell. That is, the present invention may be also applied to a case in which a cell other than a nucleated red blood cell is the target cell.

For example, the cell aligning unit 30 is not necessarily required, and may be omitted. That is, step S205 may be skipped.

What is claimed is:
1. An image processing apparatus comprising: at least one hardware processor configured to implement:

a feature value extracting unit that extracts an image feature value of an image of a cell candidate area in a captured image obtained by capturing an image of a sample including a target cell;

a discriminating unit that uses a pre-trained discriminator to identify whether or not the target cell is shown in the cell candidate area, based on the image feature value of the image of the cell candidate area;

an accepting unit that, when the cell candidate area is identified by the discriminating unit as an area in which the target cell is shown, accepts a user input from a user about whether or not the target cell is shown in the cell candidate area;

an updating unit that, when the user determines that the target cell is shown in the cell candidate area, specifies an outline area corresponding to a cell wall and updates the cell candidate area on the basis of the specified outline area so that the cell candidate area is set to a rectangle whose center is located at a centroid of a nucleus candidate area and which circumscribes the cell wall and contains the specified outline area; and a discriminator training unit that, when the user determines that the target cell is shown in the cell candidate area, trains the discriminator by using the image feature value of the image of the updated cell candidate area as a training sample based on the user input accepted by the accepting unit; and a display that, when the cell candidate area is identified by the discriminating unit as an area in which the target cell is shown, displays the image of the cell candidate area.

2. The image processing apparatus according to claim 1, wherein, when the user determines that the target cell is shown in the cell candidate area, the discriminator training unit trains the discriminator by using the image feature value of the image of the cell candidate area as a positive training sample.

3. The image processing apparatus according to claim 1, wherein, when the user determines that the target cell is not shown in the cell candidate area, the discriminator training unit trains the discriminator by using the image feature value of the image of the cell candidate area as a negative training sample.

4. The image processing apparatus according to claim 1, wherein the feature value extracting unit extracts image feature values of images of a plurality of the cell candidate areas, for each of the cell candidate areas, the discriminating unit identifies whether or not the target cell is shown in the cell candidate area, the display displays images of at least some of the cell candidate areas identified as areas in which the target cell is shown, the accepting unit accepts the user input about whether or not the target cell is shown in each of the cell candidate areas displayed by the display, the discriminator training unit trains the discriminator by using the image feature values of the images of the cell candidate areas displayed by the display as training samples, based on the user input accepted by the accepting unit, and the image processing apparatus further includes a storing unit that stores information indicating which cell candidate areas have been displayed by the display.

5. A non-transitory computer-readable storage medium storing a program for causing a computer to function as:

a feature value extracting unit that extracts an image feature value of an image of a cell candidate area in a captured image obtained by capturing an image of a sample including a target cell;

a discriminating unit that uses a pre-trained discriminator to identify whether or not the target cell is shown in the cell candidate area, based on the image feature value of the image of the cell candidate area;

a display unit that, when the cell candidate area is identified by the discriminating unit as an area in which the target cell is shown, displays the image of the cell candidate area;

an accepting unit that, when the cell candidate area is identified by the discriminating unit as an area in which the target cell is shown, accepts a user input from a user about whether or not the target cell is shown in the cell candidate area; an updating unit that, when the user determines that the target cell is shown in the cell candidate area, specifies an outline area corresponding to a cell wall and updates the cell candidate area on the basis of the specified outline area so that the cell candidate area is set to a rectangle whose center is located at a centroid of a nucleus candidate area and which circumscribes the cell wall and contains the specified outline area; and a discriminator training unit that, when the user determines that the target cell is shown in the cell candidate area, trains the discriminator by using the image feature value of the updated image of the cell candidate area as a training sample based on the user input accepted by the accepting unit.

6. An image processing method comprising:

extracting an image feature value of an image of a cell candidate area in a captured image obtained by capturing an image of a sample including a target cell;

identifying whether or not the target cell is shown in the cell candidate area, based on the image feature value of the image of the cell candidate area, by using a pre-trained discriminator;

when the cell candidate area is identified by the discriminator as an area in which the target cell is shown, displaying the image of the cell candidate area;

when the cell candidate area is identified by the discriminator as an area in which the target cell is shown, accepting a user input from a user about whether or not the target cell is shown in the cell candidate area;

when the user determines that the target cell is shown in the cell candidate area, specifying an outline area corresponding to a cell wall and updating the cell candidate area on the basis of the specified outline area so that the cell candidate area is set to a rectangle whose center is located at a centroid of a nucleus candidate area and which circumscribes the cell wall and contains the specified outline area; and when the user determines that the target cell is shown in the cell candidate area, training the discriminator by using the image feature value of the updated image of the cell candidate area as a training sample based on the accepted user input.

* * * * *